United
Dewhirst nt Number: Re. 31,624
[45] Reissued Date of Patent: Jul. 3, 1984

[54] METHOD OF TREATING INFLAMMATION

[75] Inventor: Floyd E. Dewhirst, Arlington, Mass.

[73] Assignee: Forsyth Dental Infirmary for Children, Boston, Mass.

[21] Appl. No.: 452,296

[22] Filed: Dec. 22, 1982

Related U.S. Patent Documents

Reissue of:
[64] Patent No.: 4,244,956
Issued: Jan. 13, 1981
Appl. No.: 97,506
Filed: Nov. 26, 1979

[51] Int. Cl.[3] ..... A61K 31/44; A61K 31/47; A61K 31/41; A61K 31/09

[52] U.S. Cl. ..... 424/258; 424/263; 424/273 B; 424/341; 546/152; 546/339; 548/329; 568/633; 568/644; 568/645

[58] Field of Search ..... 424/341, 258, 263, 273 B

[56] References Cited

U.S. PATENT DOCUMENTS

| | | | |
|---|---|---|---|
| 1,883,952 | 10/1932 | Klarmann et al. | 568/644 |
| 1,888,827 | 11/1932 | Klarmann et al. | 568/644 |
| 1,933,794 | 11/1933 | Eberlin et al. | 568/644 X |
| 3,182,070 | 5/1965 | Moyle et al. | 548/330 |
| 3,277,164 | 10/1966 | Haack et al. | 568/644 X |
| 3,968,143 | 7/1976 | Schact et al. | 424/317 X |
| 4,036,844 | 7/1977 | Thorne et al. | 424/263 X |
| 4,188,486 | 2/1980 | Tsukamoto et al. | 546/271 |

FOREIGN PATENT DOCUMENTS

| | | | |
|---|---|---|---|
| 2716125 | 10/1977 | Fed. Rep. of Germany | 546/34 |
| 45-12319 | 5/1970 | Japan | 546/339 |

OTHER PUBLICATIONS

Klarmann et al., J. Am. Chem. Soc., 54, pp. 1204–1211 (1932).
Cowell et al., J. Chem. Soc., (6), pp. 1082–1090 (1971).
Kurosu et al., Chemical Abstracts, vol. 89, 101973n (1978).
Jones et al., Chemical Abstracts, vol. 74, 126037p (1971).
Chemical Abstracts, vol. 89, Chemical Subject Index, p. 3938CS (1978).
Jones et al. (I), Chemical Abstracts, vol. 73, 110139s (1970).
Ferreira et al., "Ann. Rev. Phamacol.", 14: 57–73 (1974).
Wallach et al., "Biochem. Biophys. Acta.", 231: 445–457 (1971).
Winter, C.A., et al., "J. Pharmacol. Exp. Ther.", 141: 369–376 (1963).
Goldlust, M. et al., "Agents and Actions", 5: 39–47 (1975).

*Primary Examiner*—Donald G. Daus
*Assistant Examiner*—Diana G. Rivers
*Attorney, Agent, or Firm*—Richard P. Crowley

[57] ABSTRACT

A method of treating inflammation and inhibiting prostaglandin synthesis employing substituted 2-(arylmethoxy)phenol compounds.

13 Claims, No Drawings

METHOD OF TREATING INFLAMMATION

Matter enclosed in heavy brackets [ ] appears in the original patent but forms no part of this reissue specification; matter printed in italics indicates the additions made by reissue.

BACKGROUND OF THE INVENTION

Various nonsteroidal compositions, such as aspirin, phenylbutazone, indomethacin and other nonsteroidal compounds, as well as steroid compounds, such as adrenocorticosteroids, have been suggested and used as antiinflammatory agents. In addition, aminoethylphenols containing halogen and alkyl substituents have been suggested for use as antiinflammatory agents (see U.S. Pat. No. 3,928,624).

It is desirable to provide new and useful antiinflammatory agents and prostaglandins-synthetase inhibitors which are nonsteroid in nature and which avoid the disadvantages of the priorart nonsteroid and steroid compositions.

SUMMARY OF THE INVENTION

My invention relates to the treatment of inflammation by the use of substituted 2-(arylmethoxy)phenol compounds and to novel antiinflammatory compositions containing, as active ingredients, certain substituted 2-(arylmethoxy)phenol compounds.

It has been discovered that the substituted 2-(arylmethoxy)phenol compounds of this invention act as medicinal agents which inhibit the synthesis of prostaglandins, inhibit platelet aggregation and are useful as topical and systemic antiinflammatory agents. Certain of my antiinflammatory compounds are novel, while others, while not novel, have not been used or suggested for use as medicinal agents.

My invention is directed to the use of known and novel 2-(arylmethoxy)phenols and 2-(hereroarylmethoxy)phenols as antiinflammatory agents. The compounds of my invention can be represented generally by the structural formula:

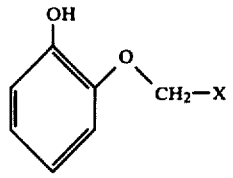

where X is a naphthyl, pyridyl, quinolyl, 2-benzimidazolyl, or substituted phenyl having the formula:

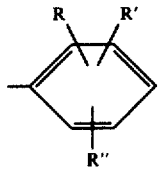

where R, R' and R'' represent hydrogen or halogen, such as chloro, fluoro, bromo or iodo radicals, lower alkyl radicals, such as $C_1$–$C_6$ alkyl radicals, such as methyl, ethyl, propyl and butyl, lower haloalkyl radicals, such as trifluoro, trichloro or tribromo methyl radicals, and lower alkoxy radicals, such as $C_1$–$C_6$ radicals, such as methoxy, ethoxy and propoxy radicals or combinations thereof and the salts thereof.

In particular, my invention concerns those preferred compounds where there are one or two substituted groups where X is a substituted phenyl radical and, more particularly, where the substituted phenyl radical contains dihalides, such as the 2,3 and 2,6 dihalo compounds. Representative compounds where X is a substituted phenyl radical include, but are not limited to: 2,3 dimethyl; 2 methyl 3 chlorol; 2 methyl 3 trichloromethyl; 2,6 dichloro; 2,5 dimethyl; 2,6 dichloro 5 methyl; 2,3 methoxy; and other compounds and the nontoxic salts thereof.

Those compounds where X represents the substituted phenyl radicals and wherein the substituent is hydrogen, parachloro, paramethoxy and 2,4 dichloro have been described in the literature for uses other than as antiinflammatory agents. For example, 2-(phenylmethoxy)phenol has been described in the literature as a bactericidal compound (Klarmann, E., L. W. Gates and V. A. Shternov, J. Am Chem. Soc. 54: 1204–1211 (1932)). 2-(4-chlorophenylmethoxy)phenol and 2-(2,4-dichlorophenylmethoxy)phenol are described in the literature as of potential use in the synthesis of sequential polypeptides (Cowell, R. D. and J. H. Jones, J. Chem. Soc. (6): 1082–1090 (1971)). Aminomethylphenols containing halogen and alkyl substituents have been described as antiinflammatory compounds in U.S. Pat. No. 3,928,624, issued Dec. 23, 1975.

My compounds may be employed alone or preferably in pharmaceutical nontoxic carrier materials in either liquid or solid form, such as in oil, alcohols; that is, as a solution, dispersion, suspension, emulsion or lotion, glycols, glycerine, starch, talc, sucrose and the like. My compounds may be employed as active antiinflammatory agents alone or in combination or with other agents, as well as in combination with those additive and supplemental materials typically employed and used in pharmaceutical compositions. My compounds may, for example, be used in those pharmaceutical compositions in the manner set forth in U.S. Pat. No. 3,928,624.

My compounds are used in the treatment of conditions in mammals (human and animal) exhibiting pain, fever and inflammation. The compounds may be administered in a variety of ways, but typically are employed in the area of pain or inflammation by topical application in a lotion, powder, solution or other form. A therapeutic amount of the 2-(arylmethoxy)phenol compound should be employed to reduce inflammation, which may range, for example, from a single to multiple treatments, such as 0.1 mg to 100 mg per kg of body weight per day; for example, 1 mg to 25 mg/kg/day. The topical composition may include from 0.001 to 5% by weight; for example, 0.01 to 1%, of the active compound.

My compounds may be incorporated in place of the aminomethylphenol compounds in the pharmaceutical compositions of U.S. Pat. No. 3,928,624.

Various standard in vitro tests have been carried out to demonstrate the effective antiinflammatory nature of my compounds, which tests can be correlated with tests in animals and humans.

The following examples are presented as illustrative of the compounds and use of such compounds in my invention.

EXAMPLE 1: 2-(2-methylphenylmethoxy)phenol (I)

For the synthesis of I, 10.0 g of a-bromo-o-xylene were added to 5.95 g of catechol dissolved in 10 ml of absolute ethanol under nitrogen. KOH, 3.3 g dissolved in 50 ml of ethanol, was added dropwise over 30 min with stirring. The solution was then refluxed under nitrogen for 2 hours. The solution was filtered to remove KBr. The solution was cooled over night and filtered to remove di-substituted product. Ethanol was removed by rotary evaporation, and the oil was dissolved in 50 ml of chloroform. The pH was adjusted to neutrality with HCl and extracted three times with equal volumes of water, to remove unreacted catechol and salts. Chloroform was removed by rotary evaporation and the oil was vacuum-distilled at 8 mm Hg. Approximately 4 g of compound I were collected in the distillate that came over at 180° C. The structure was confirmed by NMR and mass spectrum data.

EXAMPLE 2: 2-(3-chlorophenylmethoxy)phenol (II)

For the synthesis of II, 10.15 g of a,m-dichlorotoluene were added to 6.94 g of catechol dissolved in 10 ml of absolute ethanol under nitrogen. KOH, 3.45 g dissolved in 50 ml of ethanol, was added dropwise over 30 minutes with stirring. The solution was then refluxed under nitrogen for 2 hours. The solution was filtered to remove KCl. The solution was cooled over night and filtered to remove di-substituted product. Ethanol was removed by rotary evaporation, and the oil was dissolved in 50 ml of chloroform. The pH was adjusted to neutrality with HCl and extracted three times with equal volumes of water to remove unreacted catechol and salts. Chloroform was removed by rotary evaporation, and the oil was vacuum-distilled at 8 mm Hg. Approximately 4 g of compound II were collected in the distillate that came over at 190° C. The structure was confirmed by NMR and mass spectrum data.

EXAMPLE 3:
2-(3-trifluoromethylphenylmethoxy)phenol (III)

For the synthesis of III, 15.000 g of a'-chloro-aaa-trifluoro-m-xylene are added to 7.83 g of catechol dissolved in 10 ml of absolute ethanol under nitrogen. KOH, 3.99 g dissolved in 50 ml of ethanol, is added dropwise over 30 minutes with stirring. The solution is then refluxed under nitrogen for 2 hours. The solution is filtered to remove KCl. The solution is cooled over night and filtered to remove di-substituted product. Ethanol is removed by rotary evaporation, and the oil is dissolved in 50 ml extracted five times with equal volumes of water to remove unreacted catechol and salts. Chloroform is removed by rotary evaporation. The oil is vacuum-distilled at 8 mm Hg and the fraction containing III is collected.

EXAMPLE 4: 2-(4-methoxyphenylmethoxy)phenol (IV)

For the synthesis of IV, 20 g of p-methoxybenzyl bromide are added to 10.95 g of catechol dissolved in 10 ml of absolute ethanol under nitrogen. KOH, 5.58 g dissolved in 50 ml of ethanol, is added dropwise over 30 minutes with stirring. The solution is then refluxed under nitrogen for 2 hours. The solution is filtered to remove KBr. The solution is cooled over night and filtered to remove di-substituted product. Ethanol is removed by rotary evaporation, and the oil is dissolved in 50 ml of chloroform. The pH is adjusted to neutrality with HCl and extracted three times with equal volumes of water to remove unreacted catechol and salts. Chloroform is removed by rotary evaporation. The oil is vacuum-distilled at 8 mm Hg and the fraction containing IV is collected.

EXAMPLE 5: 2-(2,5-dimethylphenylmethoxy)phenol (V)

For the synthesis of V, 15.00 g of 2,5-dimethylbenzyl chloride was added to 10.68 g of catechol dissolved in 10 ml of absolute ethanol under nitrogen. KOH, 5.44 g dissolved in 50 ml of ethanol, is added dropwise over 30 minutes with stirring. The solution is then refluxed under nitrogen for 2 hours. The solution is filtered to remove KCl. The solution is cooled over night and filtered to remove di-substituted product. Ethanol is removed by rotary evaporation, and the oil is dissolved in 50 ml of chloroform. The pH is adjusted to neutrality with HCl and extracted three times with equal volumes of water to remove unreacted catechol and salts. Chloroform is removed by rotary evaporation. The oil is vacuum-distilled at 8 mm Hg and the fraction containing V is collected.

EXAMPLE 6: 2(2-naphthalenylmethoxy)phenol (VI)

For the synthesis of VI, 15.00 g of 2-(bromomethyl)-naphthalene were added to 6.94 g of catechol dissolved in 10 ml of absolute ethanol under nitrogen. KOH, 3.80 g dissolved in 50 ml of ethanol, was added dropwise over 30 minutes with stirring. The solution was then refluxed under nitrogen for 2 hours. The solution was filtered to remove KBr. The solution was cooled over night and filtered to remove di-substituted product. Ethanol was removed by rotary evaporation, and the oil was dissolved in 50 ml of chloroform. The pH was adjusted to neutrality with HCl and extracted three times with equal volumes of water to remove unreacted catechol and salts. Chloroform was removed by rotary evaporation. The oil was vacuum-distilled at 1 mm Hg and 8 g of VI were collected in the distillate that came over at 135° C.

EXAMPLE 7: 2-(2-pyridylmethoxy)phenol (VII)

For the synthesis of VII, 15.00 g of 2-picolyl chloride HCl is added to 10.07 g of catechol dissolved in 10 ml of absolute ethanol under nitrogen. KOH, 10.26 g dissolved in 100 ml of ethanol, is added dropwise over 30 minutes with stirring. The solution is then refluxed under nitrogen for 2 hours. The solution is filtered to remove KCl. The solution is cooled over night and filtered to remove di-substituted product. Ethanol is removed by rotary evaporation, and the oil is dissolved in 50 ml of chloroform. The pH is adjusted to neutrality with HCl and extracted five times with equal volumes of water to remove unreacted catechol and salts. Chloroform is removed by rotary evaporation. The oil is vacuum-distilled at 8 mm Hg and the fraction containing VII is collected.

EXAMPLE 8: 2-(2-benzimidazolylmethoxy)phenol (VIII)

For the synthesis of VIII, 15.00 g of 2-chloromethylbenzimidazole is added to 9.91 g of catechol dissolved in 10 ml of absolute ethanol under nitrogen. KOH, 5.05 g dissolved in 50 ml of ethanol, is added dropwise over 30 minutes with stirring. The solution is then refluxed under nitrogen for 2 hours. The solution is filtered to remove KCl. The solution is cooled over night and filtered to remove di-substituted product. Ethanol is removed by rotary evaporation, and the oil is dissolved in 50 ml of chloroform. The pH is adjusted to neutrality with HCl and extracted five times with equal volumes of water to remove unreacted catechol and salts. Chloroform is removed by rotary evaporation. The oil is vacuum-distilled at 8 mm Hg and the fraction containing VIII is collected.

EXAMPLE 9: 2-(2-quinolylmethoxy)phenol (IX)

For the synthesis of IX, 15.00 g of 2-(chloromethyl)-quinoline HCl are added to 7.71 g of catechol dissolved in 10 ml of absolute ethanol under nitrogen. KOH, 7.86 g dissolved in 50 ml of ethanol, is added dropwise over 30 minutes with stirring. The solution is then refluxed under nitrogen for 2 hours. The solution is filtered to remove KCl. The solution is cooled over night and filtered to remove di-substituted product. Ethanol is removed by rotary evaporation, and the oil is dissolved in 50 ml of chloroform. The pH is adjusted to neutrality with HCl and extracted five times with equal volumes of water to remove unreacted catechol and salts. Chloroform is removed by rotary evaporation. The oil is vacuum-distilled at 8 mm Hg and the fraction containing IX is collected.

The compounds of Examples 1–9 are prostaglandin synthesis inhibitors and are antiinflammatory agents.

Inhibition of prostaglandin synthesis has been shown to be the major mode of action of nonsteroidal antiinflammatory drugs (Ferrira, S. H. and Vane, J. R., Ann. Rev. Pharmacol., 14: 57–73 (1974)). A commonly used model system for examination of prostaglandin synthetase inhibition is the sheep vesicular gland microsomal preparation (Wallach, D. P. and Daniels, E. G., Biochim. Biophys. Acta., 231: 445–457 (1971)). Prostaglandin synthetase activity was determined by following oxygen tension in a closed reaction chamber using a Clark-type oxygen electrode. For each assay, 2.9 ml of 0.1 M tris HCl buffer, pH 8.0, 10 ul of 0.2 M phenol, and 50 ul of enzyme suspension (2.5 mg microsomal preparation) were added to the reaction chamber. 10 ul of inhibitor in ethanol were added 1 minute prior to initiation of the reaction. The reaction was initiated by addition of 10 ul of 3.7 mM arachidonate solution. The concentration of an inhibitor that reduced prostaglandin synthesis by 50% ($[I]_{50}$) was determined from plots of activity v. log concentration of inhibitor. The results for three 2-(arylmethoxy)phenols are given in the following Table I.

TABLE I $[I]_{50}$ Values for Inhibition of Prostaglandin Synthesis

| Compound | $[I]_{50}$ (μM) |
|---|---|
| 2-(phenylmethoxy)phenol | 5.2 |
| 2-(2-methylphenylmethoxy)phenol | 4.7 |
| 2-(3-chlorophenylmethoxy)phenol | 3.3 |

The antiinflammatory activity of these compounds is observed in various standard pharmacological tests, such as, for example, carrageenan induced foot-pad edema in rats (Winger, C. A., Risley, E. A. and Nuss, G. W., J. Pharmacol. Exp. Ther., 141: 369–376 (1963)), or the reverse passive arthus reaction in rabbits (Goldlust, M. R. and Schreiber, W. F., Agents and Actions, 5: 39–47 (1975)).

Inhibition of platelet aggregation by prostaglandin synthetase inhibitors is of potential value in treating thromboembolic disorders. Aggregation experiments were performed in a single-channel Chrono-log Platelet Aggregometer at 37° C. To 500 ul of platelet-rich plasm were added 2 ul of inhibitor solution and 50 ul of 10 mM arachidonate. The $[I]_{50}$ value was defined as the concentration of inhibitor which prevented irreversible aggregation 50% of the time. The $[I]_{50}$ of 2-(phenylmethoxy)-phenol was 0.57 uM.

My antiinflammatory compounds may be employed in typical antiflammatory compositions, to replace hexylresorcinol in troches and lozenges and other medicinal materials, as the active or supplemental ingredients in the treatment of acne, in antibacterial, antifungal and antiitching preparations, as a nonnarcotic analgesic and for aid in the treatment of thromboembolic disorders.

What I claim is:

1. A method of treating inflammation in mammals, which method comprises administering to the mammal a therapeutical effective amount of a compound of the formula:

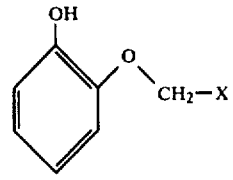

where X is selected from the group consisting of:

(a) naphthyl, pyridyl, quinolyl and 2-benzimidazolyl; and (b) *phenyl radical or* a *mono or di* substituted phenyl having [the structural formula

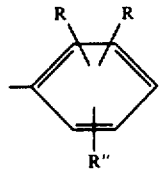

where R, R' and R'' are hydrogen,] *radical substituent groups selected from the group consisting of* halogen, $C_1$–$C_6$ alkyl, $C_1$–$C_6$ haloalkyl, $C_1$–$C_6$ alkoxy or combinations thereof and the nontoxic pharmaceutically acceptable salts thereof.

[2. The method of claim 1 wherein R' and R'' are halogen radicals and R is hydrogen.]

[3. The method of claim 1 wherein R is a hydrogen, R' is a methyl radical and R'' is a chloro radical.]

[4. The method of claim 1 wherein R is hydrogen, R' is a trihalomethyl radical and R'' is a methyl radical.]

[5. The method of claim 1 wherein R is hydrogen and R' and R'' are methyl radicals.]

[6. The method of claim 1 wherein R and R' are chloro radicals and R'' is a methyl radical.]

[7. The method of claim 1 wherein R and R' are methyl radicals and R'' is hydrogen.]

[8. The method of claim 1 wherein R and R' are methoxy radicals and R'' is hydrogen.]

9. The method of claim 1 wherein the compound is selected from the group consisting of: 2-(2-methylphenylmethoxy)phenol; 2-(3-chlorophenylmethoxy)-phenol; 2-(3-trifluoromethylphenylmethoxy)phenol; 2-(4-methoxyphenylmethoxy)phenol; 2-(2,5-dimethylphenylmethoxy)phenol; 2-(2-naphthalenylmethoxy)- phenol; 2-(2-pyridylmethoxy)phenol; 2-(2-benzimidazolylmethoxy)phenol; and 2-(2-quinolylmethoxy)phenol.

10. The method of claim 1 which comprises applying topically to the inflammed area a pharmaceutical composition containing a pharmaceutically acceptable carrier material and from about 0.001 to 5% by weight of the compound.

11. A pharmaceutical composition for the treatment of inflammation, which composition comprises a pharmaceutically accepted carrier material and from about 0.001% to 5% by weight of a 2-(arylmethoxy)phenol compound selected from the group consisting of:

(a) 2-(2-methylphenylmethoxy)phenol;
(b) 2-(3-chlorophenylmethoxy)phenol;
(c) 2-(3-trifluoromethylphenylmethoxy)phenol;
(d) 2-(4-methoxyphenylmethoxy)phenol;
(e) 2-(2,5-dimethylphenylmethoxy)phenol;
(f) 2-(2-naphthalenylmethoxy)phenol;
(g) 2-(2-pyridylmethoxy)phenol;
(h) 2-(2-benzimidazolylmethoxy)phenol; and
(i) 2-(2-quinolylmethoxy)phenol and their pharmaceutically accepted salts.

*12. The method of claim 1 wherein the substituent group is a methyl group.*

*13. The method of claim 1 wherein the substituent group is a halogen group.*

*14. The method of claim 13 wherein the substituent group is a chloro group.*

*15. The method of claim 1 wherein the substituent group is a methoxy group.*

*16. The method of claim 1 wherein the substituent group is a tri halomethyl group.*

*17. The method of claim 1 wherein the compound is a di substituted 2-(phenylmethoxy)phenol compound and wherein one substituent group is a methyl group and another substituted group is a halogen group.*

*18. The method of claim 1 wherein the compound is a di substituted 2-(phenylmethoxy)phenol compound and both substituent groups are methyl groups.*

*19. The method of claim 1 wherein the compound is a di substituted 2-(phenylmethoxy)phenol compound and both substituent groups are methoxy groups.*

*20. The method of claim 1 wherein the compound is a di substituted 2-(phenylmethoxy)phenol compound and one substituted group is a methyl group and another substituted group is a tri halomethyl group.*

* * * * *